(12) United States Patent
Struck

(10) Patent No.: US 11,975,049 B2
(45) Date of Patent: *May 7, 2024

(54) THERAPEUTIC TREATMENT FOR NEUROTROPHIC KERATOPATHY

(71) Applicant: Michael C. Struck, Madison, WI (US)

(72) Inventor: Michael C. Struck, Madison, WI (US)

(73) Assignee: Michael Struck, Madison, WI (US)

( * ) Notice: Subject to any disclaimer, the term of this patent is extended or adjusted under 35 U.S.C. 154(b) by 170 days.

This patent is subject to a terminal disclaimer.

(21) Appl. No.: 17/176,810

(22) Filed: Feb. 16, 2021

(65) Prior Publication Data
US 2021/0236604 A1 Aug. 5, 2021

Related U.S. Application Data

(63) Continuation of application No. 15/928,293, filed on Mar. 22, 2018, now Pat. No. 10,918,699.

(60) Provisional application No. 62/474,826, filed on Mar. 22, 2017.

(51) Int. Cl.
| | |
|---|---|
| *A61K 38/28* | (2006.01) |
| *A61K 9/00* | (2006.01) |
| *A61K 9/08* | (2006.01) |
| *A61K 38/30* | (2006.01) |
| *A61P 27/02* | (2006.01) |

(52) U.S. Cl.
CPC ............ *A61K 38/28* (2013.01); *A61K 9/0048* (2013.01); *A61K 9/0051* (2013.01); *A61K 9/08* (2013.01); *A61K 38/30* (2013.01); *A61P 27/02* (2018.01)

(58) Field of Classification Search
CPC ........ A61K 9/0048; A61K 38/28; A61P 27/02
See application file for complete search history.

(56) References Cited

U.S. PATENT DOCUMENTS

| | | | |
|---|---|---|---|
| 7,829,532 B2 | 11/2010 | Gardner et al. | |
| 2012/0003296 A1* | 1/2012 | Shantha | A61P 27/02 514/5.9 |
| 2013/0210761 A1* | 8/2013 | Baker | A61P 11/00 514/54 |
| 2015/0094260 A1 | 4/2015 | Braiman-wiksman et al. | |

OTHER PUBLICATIONS

Wang et al. (2016).*
Zagon IS, et al., "Use of Topical Insulin to Normalize Corneal Epithelial Healing in Diabetes Mellitus" Arch Ophthalmol. 2007;125(8):1082-1088.
Klocek MS, et al., "Naltrexone and Insulin Are Independently Effective but Not Additive in Accelerating Corneal Epithelial Healing in Type I Diabetic Rats" Exp Eye Res. 2009;89(5):686-692.
Aynsley TR. "The Use of Insulin in the Treatment of Corneal Ulcers" Br J Ophthalmol. 1945;29(7):361-363.
Chen DK, et al., "Repeated monitoring of corneal nerves by confocal microscopy as an index of peripheral neuropathy in type-1 diabetic rodents and the effects of topical insulin." J Peripher Nerv Syst. 2013;18(4):306-315.
Shanley LJ, et al., "Insulin, Not Leptin, Promotes In Vitro Cell Migration to Heal Monolayer Wounds in Human Corneal Epithelium" Invest Ophthalmol Vis Sci. 2004;45(4):1088-1094.
Nishida T, et al., "Advances in treatment for neurotrophic keratopathy" Curr Opin Ophthalmol. 2009;20(4):276-281.

* cited by examiner

*Primary Examiner* — Gyan Chandra
(74) *Attorney, Agent, or Firm* — J. Mitchell Jones; Casimir Jones, S.C.

(57) ABSTRACT

The invention provides reagents, pharmaceutical compositions and methods for the treatment of prevention of disorders and diseases related to defects in trigeminal innervation of the cornea, stem cell deficiency, nonhealing epithelial wounds and particularly to diseases such as neurotrophic keratopathy.

6 Claims, 1 Drawing Sheet

THERAPEUTIC TREATMENT FOR NEUROTROPHIC KERATOPATHY

CROSS-REFERENCE TO RELATED APPLICATIONS

This application is a continuation of U.S. patent application Ser. No. 15/928,293, filed Mar. 22, 2018, allowed as U.S. Pat. No. 10,918,699, which claims priority to U.S. Provisional Patent Application No. 62/474,826, filed Mar. 22, 2017, the contents of which are incorporated by reference in their entireties.

FIELD OF THE INVENTION

The invention provides reagents, pharmaceutical compositions and methods for the treatment of prevention of disorders and diseases related to defects in trigeminal innervation of the cornea, stem cell deficiency, nonhealing epithelial wounds and particularly to diseases such as neurotrophic keratopathy.

BACKGROUND OF THE INVENTION

Neurotrophic keratopathy is a degenerative disease of the corneal epithelium secondary to impaired corneal innervation by the trigeminal nerve. Standard treatment involves aggressive lubrication of the corneal surface, therapeutic contact lenses, amniotic membrane grafts and tarsorrhaphy. Refractory neurotrophic corneal ulcers occur when treatment response is incomplete and are potentially blinding.

What is needed in the art are new methods of treating and preventing diseases such as neurotrophic keratopathy.

SUMMARY OF THE INVENTION

The invention provides reagents, pharmaceutical compositions and methods for the treatment of prevention of disorders and diseases related to defects in trigeminal innervation of the cornea, and particularly to diseases such as neurotrophic keratopathy.

Accordingly, in some embodiments, the present invention provides methods of treating or preventing a refractory ocular epithelial defect comprising: contacting the eye of a subject diagnosed with a refractory ocular epithelial defect with an insulin agent in an ophthalmologically acceptable carrier in amount effective to treat or prevent the refractory ocular epithelial defect. In some embodiments, the insulin agent is recombinant human insulin. In some embodiments, the insulin agent is selected from, for example, IGF-I and IGF-II. In some embodiments, the insulin agent is an insulin mimetic. In some embodiments, the subject has a defect in trigeminal innervation of the cornea. In some embodiments, the subject has a neurotrophic corneal ulcer. In some embodiments, the subject has a deficiency in epithelial healing mechanism. In some embodiments, the subject has a deficiency in epithelial stem cell function. In some embodiments the subject has a chemical burn. In some embodiments, the neurotrophic corneal ulcer is refractory. In some embodiments, the treatment results in greater than 95% (e.g., greater than 95%, 96%, 97%, 98%, 995, or fractions thereof) corneal re-epithelialization. In some embodiments, the treatment results in essentially complete corneal re-epithelialization.

In some embodiments, the present invention provides methods of treating neurotrophic corneal ulcer in a subject in need thereof comprising: contacting the eye of a subject with a neurotrophic corneal ulcer with an insulin agent in an ophthalmologically acceptable carrier in amount effective to cause healing of said neurotrophic corneal ulcer. In some embodiments, the insulin agent is recombinant human insulin. In some embodiments, the insulin agent is selected from, for example, IGF-I and IGF-II. In some embodiments, the insulin agent is an insulin mimetic. In some embodiments, the subject has a defect in trigeminal innervation of the cornea. In some embodiments, the neurotrophic corneal ulcer is refractory. In some embodiments, the treatment results in greater than 95% (e.g., greater than 95%, 96%, 97%, 98%, 995, or fractions thereof) corneal re-epithelialization. In some embodiments, the treatment results in essentially complete corneal re-epithelialization.

In some embodiments, the present invention provides for the use of an insulin agent to treat or prevent a refractory ocular epithelial defect selected from, for example, a neurotropic keratopathy, an epithelial stem cell deficiency, a non-healing epithelial wound, or a chemical burn in a subject diagnosed with neurotrophic keratopathy.

In some embodiments, the present invention provides for the use of an insulin agent to treat or prevent neurotrophic corneal ulcers in a subject diagnosed with neurotrophic keratopathy.

In some embodiments, the present invention provides for the use of an insulin agent to treat non-healing or slowly healing ophthalmologic epithelial defects.

Further embodiments provide an insulin agent for use in treating or preventing a refractory ocular epithelial defect selected from, for example, a neurotropic keratopathy, an epithelial stem cell deficiency, a non-healing epithelial wound, or a chemical burn in a subject diagnosed with neurotrophic keratopathy.

Additional embodiments are described herein.

DESCRIPTION OF THE INVENTION

Figures 1A, 1B:
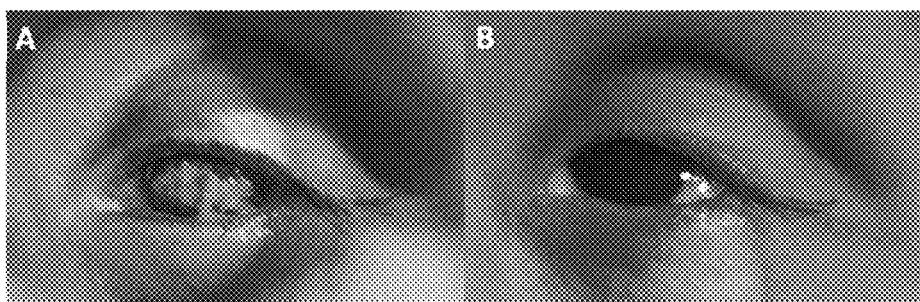
FIG. 1A-F shows results of three patients treated with topical insulin. A 2-year-old girl with proptosis and lagophthalmos from an orbital teratoma presented with a neurotrophic corneal ulcer refractory to lubrication and permanent lateral tarsorrhaphy (A). Insulin eye drops were initiated with resolution of the ulcer after 14 days (B). A 24-year-old woman with neurotrophic keratopathy secondary to herpes zoster keratitis presents with a corneal ulcer refractory to lubrication and use of scleral contact lens (C). Insulin drops were initiated with resolution of the ulcer after 25 days (D). A 47-year-old woman with neurotrophic keratopathy secondary to cranial nerve injury presents with near descemetocele in the central cornea of the left eye (E). Insulin drops were initiated with resolution of the ulcer after 7 days (F).

The invention provides reagents, pharmaceutical compositions and methods for the treatment of prevention of disorders and diseases related to defects in trigeminal innervation of the cornea, stem cell deficiency, nonhealing epithelial wounds and particularly to diseases such as neurotrophic keratopathy. The method specifically comprises periocular administration of insulin, insulin-like molecules, insulinomimetic agents or peptides via topical, subconjunctival, or sub-Tenon's routes.

More specifically, the method of the invention comprises treating or preventing neurotrophic keratopathy and to treating ulcers in subjects diagnosed with neurotrophic keratopathy or improper trigeminal innervation of the cornea by periocularly administering a sufficient amount of a formulation of insulin, insulin-like mocleules, insulinomimetic agents or peptides to one or both eyes.

Specifically, the inventive methods comprise direct insulin, insulin-like molecule or insulin mimetic (together referred to as insulin agents) administration to the eye, and specifically to the cornea and conjunctiva. Any pharmaceutically acceptable insulin or insulin mimetic formulation can be used with the methods of the invention. Examples of useful insulin formulations include native insulin (preferably human insulin, particularly recombinantly-produced human insulin such as Humulin™, or insulin isolated from any other mammalian species), naturally derived or recombinant, and all of modifications thereof, such as insulin NPH, Ultralente (Eli Lilly & Co.), insulin glargin (Lantus™, Aventis), Lispro™, (Eli Lilly & Co.), Novolin™ (Novo-Nordisk) and formulations containing any modifying proteins (such as, for example, prolamine) or buffers known or accepted in the art.

Moreover, the invention provides methods comprising administration of insulin-like molecules, insulinomimetic agents or nucleotides (aptamers) that mimic some or all of insulin's action. Insulin-like molecules include, but are not limited to, insulin-like growth factor I (IGF-I) and insulin-like growth factor II (IGF-II). The invention further encompasses the administration of drugs that augment insulin along with the insulin. These augmenting drugs can be, inter alia, from the thiazolidinediones (TZD) class. They may also be small non-peptide insulinomimetic agents such as TLK16998 (Telik), KRX-613, and L-783,281 (Merck). Such compounds activate the proliferator-activator gamma (PPAR-gamma) receptor to provide necessary actions of insulin in the epithelium.

Concentrations of the drugs used in the invention can range in micromolar concentrations. If the drug is a liquid or gel insulin formulation, volumes can range from about 0.05 ml to about 1 mL. A sufficient dosage of the insulin ranges from 0.05 units to 1 unit.

The inventive treatment provided herein permits a number of different administration routes to be used to introduce an effective amount of a drug to the eye. These include administering the drug via a pump, a polymeric base, or a solution. The preferred method of administration is by a solution. Additionally, drugs may be administered by implantation of a formulation of the invention or a device that will release such a formulation at a prescribed rate. The invention advantageously provides methods for administering said formulation to both eyes simultaneously, although embodiments having administration to one eye, as well as embodiments having independent or non-contemporaneous administration to both eyes, are also encompassed by the invention.

The insulin agents may be administered to a patient needing treatment in combination with an ophthalmologically-acceptable vehicle or carrier. Other components, which may be included in the carrier components include, without limitation, buffer components, tonicity components, preservative-components, pH adjustors, components commonly found in artificial tears, such as one or more electrolytes, and the like and mixtures thereof. In one very useful embodiment the carrier component includes at least one of the following: an effective amount of a buffer component; an effective amount of a tonicity component; an effective amount of is a preservative component; and water.

These additional components preferably are ophthalmologically acceptable and can be chosen from materials which are conventionally employed in ophthalmic compositions, for example, artificial tear formulations and the like.

Acceptable effective concentrations for these additional components in the compositions of the invention are readily apparent to the skilled practitioner.

Accordingly, the insulin agent may be administered, alone, or in combination with pharmaceutically acceptable substances including buffer solutions, for example phosphate buffered saline, or inert carrier compounds, glycerols, mineral oils, collagen, colloids, contact lenses or similar substances to the ocular surface of the eye.

Additional therapeutic agents may be co-administered or delivered with the insulin agent. Exemplary therapeutic agents that are used in conjunction with the insulin agent in the method of the present invention include, but are not limited to NMDA antagonists, antihistamines, antiparasitics, miotics, sympathomimetics, anticholinergics, local anesthetics, amoebicidals, trichomonocidals, mydriatics, carbonic anhydrase inhibitors, ophthalmic diagnostic agents, ophthalmic agents used as adjuvants in surgery, chelating agents, antineoplastics, diagnostics, adrenergic anesthetics, beta blockers, alpha-2-agonists, cycloplegics, prostaglandins, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity, anti-viral drugs, e.g. acyclovir, gancyclovir, vidarabine, azidothymidine, dideoxyinosine, dideoxycytosine, dexamethasone, ciproflaxin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, keterolac, naproxen, etc., an anesthetic, e.g. lidocaine; beta-adrenergic blocker or beta-adrenergic agonist, e.g. ephidrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine; antiamebic agents, e.g. chloroquine and chlortetracycline; and antifungal agents, e.g. amphotericin, etc., anti-angiogenesis compounds such as anecortave acetate, anti-glaucoma agents, such as brimonidine, acetozolamide, bimatoprost, Timolol, mebefunolol; memantine; alpha-2 adrenergic receptor agonists; 2ME2; anti-neoplastics, such as vinblastine, vincristine, interferons; alpha., beta. and .gamma., antimetabolites, such as folic acid analogs, purine analogs, and pyrimidine analogs; immunosuppressants such as azathiprine, cyclosporine and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like, including derivatives thereof and mixtures thereof.

Drug formulations of the invention advantageously can be administered to the surface or under the mucous membrane of the eye or the Tenon's fascia of the eye. More specifically, the drugs can be delivered to the subconjunctival and/or sub-Tenon's space.

The inventive methods for treatment of trigeminal nerve-related disorders, such as neurotrophic keratopathy, are suitable for prevention or treatment at any stage of such trigeminal nerve-related disorders. Specifically, the inventive methods are equally effective for prevention as well as treatment of neurotrophic keratopathy and related conditions such as neurotrophic corneal ulcers and especially refractory corneal ulcers.

EXAMPLES

The following Examples are intended to further illustrate certain aspects of the above-described method and advantageous results. The following examples are shown by way of illustration and not by way of limitation.

Example 1

The purpose of this study is to present 6 patients with refractory neurotrophic corneal ulcers that were treated with topical insulin.

Methods. A retrospective chart review of 6 patients at the University of Wisconsin was conducted. All patients were prescribed insulin drops for the treatment of neurotrophic corneal ulcers. Unless otherwise noted, the drops were prepared by mixing regular insulin in artificial tears with a polyethylene glycol and propylene glycol base at a concentration of 1 unit per mL. The drops were refrigerated and used up to 1 month after preparation.

Results. Case 1: A 2-year-old girl with a history of an excised teratoma involving the left orbit resulting in proptosis and lagophthalmos presented with a large corneal ulcer of the left eye. The ulcer measured 7×4 mm on presentation. Corneal sensation was absent in the affected eye. After 5 months of aggressive treatment, including permanent lateral tarsorrhaphy and inferior rectus recession to encourage Bell's phenomenon, the ulcer remained. The patient was started on topical insulin drops 3 times daily. After 14 days of treatment, the ulcer had healed completely. The insulin was tapered to once daily. At 18 month follow-up, the corneal epithelium remained intact.

Case 2: A 2-year-old boy with a history of aniridia, epithelial stem cell deficiency and surgically controlled bilateral congenital glaucoma presented with a corneal epithelial defect measuring 5×6.5 mm in the left eye (FIG. 1A). Formal corneal sensation testing was not performed; however, the patient's cornea was presumed to be hypesthetic as he was asymptomatic. The patient was treated with antibiotic ointment and amniotic membrane grafting twice. After 5 months with persistent epithelial defect, insulin drops were started 3 times daily. After 13 days of treatment, the corneal epithelium had healed completely (FIG. 1B) and the drop was tapered to twice daily. The patient has had no recurrent epithelial defect 1 year since starting the treatment.

Figures 1C, 1D:
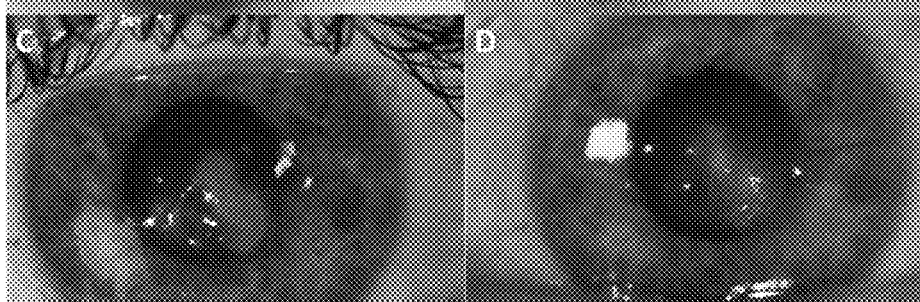

Case 3: A 24-year-old woman with a history of herpes zoster keratoconjunctivitis and neurotrophic keratopathy in the left eye presented with a persistent epithelial defect and mild ulceration. She developed the defect, which measured 3×2 mm, despite daily use of a scleral contact lens (FIG. 1C). Insulin drops were started twice daily and at 2 week follow-up, the defect improved to 1×1 mm. After another 2 weeks, the epithelial defect had resolved, with some residual epithelial irregularity (FIG. 1D). The patient used the insulin drops a total of 25 days; they were discontinued and follow-up was transferred when she moved out of state.

Figures 1E, 1F:
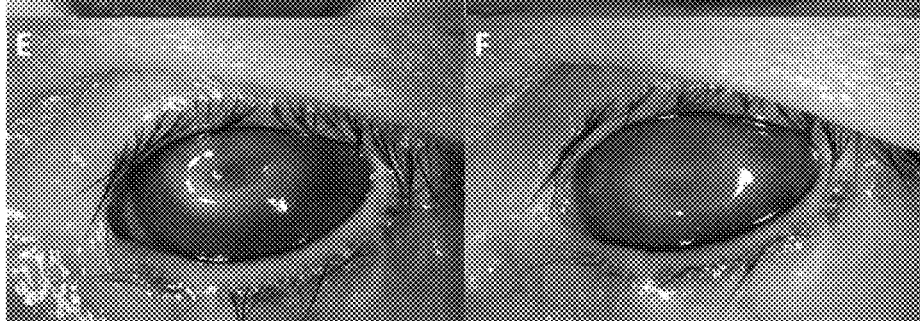

Case 4: A 47-year-old woman with a history of neurotrophic keratopathy in both eyes secondary to cranial nerve injury and a large corneal scar in the left eye from a previous ulcer, presents with a near descemetocele in the central cornea of the left eye. The area of thinning measured 1.5×2.5 mm on presentation (FIG. 1E). The patient had previously had a surgical tarsorrhaphy in the left eye. She was diabetic on lispro insulin and was started on insulin drops (2 Units of lispro in 10 mL of artificial tears) 2-3 times daily. After 7 days of treatment, the ulcer had healed completely with thickened epithelium over the previous descemetocele (FIG. 1F). The drops were used a total of 3 weeks and were discontinued secondary to patient preference.

Case 5: A 71-year-old woman presents with a non-healing, asymptomatic 4×4 mm epithelial defect following vitrectomy. She was treated with lubrication, bandage contact lens and amniotic membrane graft with minimal improvement over the course of 4 months. Insulin drops were started twice and after 14 days of treatment, the epithelial defect had resolved. The patient was tapered to insulin drops once daily, then self-discontinued the drops after several months. At 1 year follow-up, the epithelium remained intact with no recurrent defect.

Case 6: A 73-year-old woman with a history of herpes zoster neurotrophic keratopathy presents with non-healing epithelial defect of the left eye. She was treated with amniotic membrane three times, temporary tarsorrhaphy, and chronic topical steroid therapy. After two months, the defect persisted at 1.5×2.5 mm, and the patient was started on insulin drops 3 times daily. After 8 days of treatment, the epithelial defect had resolved. Four months after initial presentation, the patient developed a large infectious ulcer and crystalline keratopathy. She was continued on insulin drops during this time with the epithelial defect slowly improving in size. Three months after development of the crystalline keratopathy, the patient had a flare of zoster keratitis and the insulin drops were discontinued.

Case 7: A 21 year old diabetic woman with uncontrolled diabetes type 1 since 2 years of age was diagnosed with non-healing corneal defect. She was treated with insulin drops 3 times daily. After 2 weeks of treatment the epithelial defects had resolved.

Conclusions. This Example describes 7 patients who developed neurotrophic corneal ulcers or epithelial defects that were refractory to a range of standard medical and surgical treatments. The addition of topical insulin resulted in rapid and complete corneal re-epithelialization ranging from 7 to 25 days following initiation of treatment. One patient developed crystalline keratopathy while on the treatment, though this was likely secondary to chronic topical steroid use. No other local or systemic side effects were noted, including change in corneal vascularization or opacity.

Topical insulin has been found to improve healing of decubitus ulcers (Van Ort S R, Gerber R M. Nurs Res. 1976; 25(1):9-12) and experimentally-induced superficial skin wounds in diabetic and non-diabetic individuals (Greenway S E, et al., *J Wound Care*. 1999; 8(10):526-528). The effect of topical insulin on corneal wound healing has been well-studied in rodent models. Notably, in diabetic rats, topical insulin improves corneal sensation (Zagon I S, et al., *Arch Ophthalmol*. 2007; 125(8):1082-1088) and improves wound healing after corneal abrasions (Zagon et al., supra; Klocek M S, et al., *Exp Eye Res*. 2009; 89(5):686-692). Experience with insulin in corneal wound healing in humans is limited to a 1945 case series that reported improved healing of corneal ulcers after systemic administration of insulin (Aynsley T R. *Br J Ophthalmol.* 1945; 29(7):361-363).

The mechanism of insulin in promoting cornea wound healing in our patients remains speculative, but data suggest that restoration of corneal nerves and/or improved epithelial cell migration may play key roles. In diabetic mice, topical insulin has been shown to slow the loss of sub-basal plexus corneal nerves (Chen D K, et al., *J Peripher Nerv Syst.* 2013; 18(4):306-315). Furthermore, the addition of insulin promoted cell migration and closure of artificial wounds in cultured sheets of corneal epithelial cells in an in vitro model of corneal epithelial wound healing (Shanley L J, et al., *Invest Ophthalmol Vis Sci.* 2004; 45(4):1088-1094).

Insulin-like growth factor-1 (IGF-1) has been shown to be an important modulator of corneal wound healing. In several pre-clinical studies, IGF-1 was shown to act synergistically with substance-P to promote corneal epithelium wound healing (Nishida T, et al., *Curr Opin Ophthalmol.* 2009; 20(4):276-281). In two case series, patients with neurotrophic corneal epithelial defects treated with a topical combination of substance P-derived peptides and either IGF-1 or IGF-1-derived peptides underwent complete epithelial resurfacing within 4 weeks, at response rates of 89% (Nishida T, et al., *Jpn J Ophthalmol.* 2007; 51(6):442-447) and 73% (Yamada N, et al., *Br J Ophthalmol.* 2008; 92(7): 896-900).

What is claimed is:

1. A method of treating neurotrophic corneal ulcer in a subject in need thereof comprising:
   contacting the eye of a subject with a neurotrophic corneal ulcer with a formulation consisting essentially of insulin in an opthamologically acceptable carrier in amount effective to cause healing of said neurotrophic corneal ulcer.

2. The method of claim 1, wherein said insulin is recombinant human insulin.

3. The method of claim 1, wherein said subject has a defect in trigeminal innervation of the cornea.

4. The method of claim 1, wherein said neurotrophic corneal ulcer is refractory.

5. The method of claim 1, wherein said treatment results in greater than 95% corneal re-epithelialization.

6. The method of claim 1, wherein said treatment results in essentially complete corneal re-epithelialization.

* * * * *